(12) United States Patent
Rovaniemi (10) Patent No.: US 8,142,410 B2
(45) Date of Patent: Mar. 27, 2012

(54) FLUID ABSORPTION MAT (75) Inventor: Rolf Rovaniemi, Kisa (SE)

(73) Assignee: Absorbest, AB, Kisa (SE)

( * ) Notice: Subject to any disclaimer, the term of this patent is extended or adjusted under 35 U.S.C. 154(b) by 327 days.

(21) Appl. No.: 12/441,157

(22) PCT Filed: Sep. 14, 2006

(86) PCT No.: PCT/SE2006/001050
§ 371 (c)(1),
(2), (4) Date: May 27, 2009

(87) PCT Pub. No.: WO2008/033061
PCT Pub. Date: Mar. 20, 2008

(65) Prior Publication Data
US 2010/0036345 A1 Feb. 11, 2010

(51) Int. Cl.
*A61F 13/15* (2006.01)
(52) U.S. Cl. ............... 604/385.101; 604/378; 604/380; 428/95; 428/156; 428/163
(58) Field of Classification Search ........... 604/385.101, 604/378, 380; 428/95, 156, 163
See application file for complete search history.

(56) References Cited

U.S. PATENT DOCUMENTS

| | | | |
|---|---|---|---|
| 4,295,987 A | 10/1981 | Parks | |
| 4,328,275 A | 5/1982 | Vargo | |
| 4,609,580 A | 9/1986 | Rockett | |
| 4,865,886 A | 9/1989 | Itoh | |
| 5,028,468 A | 7/1991 | Taylor | |
| 5,173,346 A | 12/1992 | Middleton | |
| 5,434,339 A | 7/1995 | La Motte | |
| 6,759,353 B2 | 7/2004 | Eriksen | |
| 2002/0037387 A1 | 3/2002 | Sweeney | |
| 2003/0099576 A1 | 5/2003 | Li | |
| 2003/0227106 A1 | 12/2003 | Fuller | |
| 2004/0131820 A1* | 7/2004 | Turner et al. | 428/92 |
| 2004/0226834 A1 | 11/2004 | Baldwin, Jr. | |
| 2004/0261209 A1 | 12/2004 | McKay | |
| 2005/0009425 A1 | 1/2005 | Foote | |
| 2005/0191462 A1 | 9/2005 | Baldwin, Jr. | |
| 2006/0029773 A1 | 2/2006 | Waterman | |

FOREIGN PATENT DOCUMENTS

| | | |
|---|---|---|
| JP | 2001178742 A | 7/2001 |
| SE | 512624 C2 | 4/2000 |
| WO | 9641561 A1 | 12/1996 |
| WO | 2005016085 | 2/2005 |

OTHER PUBLICATIONS

DryMax XL (2 pages).
International Search Report dated Mar. 3, 2007 to corresponding PCT application No. PCT/SE2006/001050 (4 pages).

\* cited by examiner

*Primary Examiner* — Jacqueline F. Stephens
(74) *Attorney, Agent, or Firm* — Maier & Maier, PLLC (57) ABSTRACT

A fluid absorption mat for use in a medical environment, the fluid absorption mat being a substantially planar mat having at least one fluid absorption layer. At least two absorption portions, presenting substantially juxtaposed projections on a principle plane of the mat, and present different absorption capacities are provided. Furthermore, use of the fluid absorption mat in a medical environment is provided.

17 Claims, 8 Drawing Sheets

FLUID ABSORPTION MAT

RELATED APPLICATIONS

This application claims priority, under 35 U.S.C. §119, to International Patent Application No.: PCT/SE2006/01050, filed on Sep. 14, 2006, the disclosure of which is incorporated by reference herein in its entirety.

TECHNICAL FIELD OF THE INVENTION

The present invention generally relates to a fluid absorption mat for absorption of fluids, such as absorption of body fluids and irrigation solutions (flushing agents), in medical room environments. The invention also relates to uses of such a fluid absorption mat.

TECHNICAL BACKGROUND

Using a disposable fluid absorption mat for absorption of fluids spillage in different environments, such as absorption of body fluids and irrigation solutions (flushing agents) in medical room environments, is already known.

A well-known fluid absorption mat consists of an upper layer of cellulose and a bottom layer of a polyethene barrier. Such a mat is applied on the floor in an area into which fluids can drip or flow and on which a person is standing during surgery, for example. The mat is suitable for absorbing irrigation solutions, blood, urine and the same. The mat provides a floor mat on which a medical person is standing without the risk to slip and fall. The barrier layer is provided to prevent any leakage of fluids reaching the floor, minimizing the risk of a wet and slippery floor. Notwithstanding, such a mat has a limiting absorption capacity and consequently the mat easily becomes saturated with fluids during application, leading to the risk of fluid leakage and a wet and slippery floor, and to the risk of contaminating the floor with hazardous fluids.

A further known fluid absorption mat comprises a polymer having a high absorption capacity, normally referred to as a super absorbent polymer. An example of such a polymer is sodium polyacrylate, which is also known for use in diapers. U.S. Pat. No. 5,434,339 discloses a fluid absorption floor mat comprising a super absorbent polymer. The floor mat consists of an upper layer and bottom layer made from a fluid absorbing non-woven, non-cellulose fibrous material and an intermediate containing a fluid absorbent and retaining cross-linked polyacrylic acid/polyalcohol grafted copolymer interlocked between the two fibrous layers. This floor mat is provided to absorb liquids and to retain the absorbed liquids, even when pressure, such as the weight of a person, is exerted on the mat. Notwithstanding, there is still a risk of leakage or migration of fluids, especially a formed gel of the super absorbent polymers having absorbed the fluids, from such a floor mat having a high absorption capacity, especially upon exerted pressure on the mat during its application. This might in turn lead to a floor mat surface that is slippery and to the risk of contaminating the environment in the vicinity of the floor mat in use. Furthermore, there is a risk of gel contamination of a shoe sole on a person standing on the floor mat in use, which in turn might cause the person to contaminate floor areas out of the floor mat with the gel. This might also cause the person to slip and fall, especially if the person after being contaminated with the gel moves from the mat in use into areas out of the floor mat.

Thus, a problem associated with prior-art fluid absorption mats is the risk of leakage of gel and/or super absorbent polymers, which in turn might cause undesired fluid contamination in the medical environment in which the mat is used, and which, for example, might cause a person to slip and fall.

Therefore, there is a need for an improved fluid absorption mat.

SUMMARY OF THE INVENTION

In view of the aforementioned respects of known fluid absorption mats, an object of the present invention is to provide an improved fluid absorption mat.

The object is wholly or partially achieved by a fluid absorption mat and a use of such a mat according to the respective independent claim. Embodiments are set forth in the appended dependent claims, in the following description and in the drawings.

According to a first aspect of the invention there is provided a fluid absorption mat for use in a medical environment. The fluid absorption mat is a substantially planar mat having at least one fluid absorption layer. The fluid absorption mat is characterized in that at least two absorption portions, presenting substantially juxtaposed projections on a principle plane of the mat, present different absorption capacities.

Absorption capacity here means the capacity expressed in maximum absorbed amounts of fluids per area unit of the fluid absorption mat or the absorption portion of the mat without pressure exerted on the mat or the absorption portion.

Presenting substantially juxtaposed projections here means that the absorption portions are joined together so as to present the juxtaposed projections. As should be appreciated, the fluid absorption mat, and also the absorption portions are substantially planar. This means that a partially planar overlapping of the planar absorption portions may be allowed, depending on the means for joining the absorption portions. The planar portions may also be placed edge to edge. Accordingly, the mat can be produced by joining the separate absorption portions, by attaching one edge of an absorption portion to an edge of another absorption portion, in an edge-to-edge manner or in an overlapping manner. Furthermore, the mat may also be produced as a single unit, wherein the absorption portions are comprised in the unit. The portions may have different thicknesses.

The arrangement of several absorption portions provides a high fluid absorption capacity, and reduces or eliminates the risk of fluid leakage and/or contamination of an environment in which the mat is used. The arrangement of several portions also provides a non-slip mat that reduces or eliminates the risk of a mat or a surrounding area, in which the mat is used, being slippery. For example, the arrangement of several portions provides an absorption portion having a low absorption capacity having outer facing surfaces that reduces the risk of the portion being slippery when pressure, such as the weight of a person, is exerted on the absorption portion. The arrangement also provides a possibility to direct the fluid to be absorbed from specific areas in the place of use. For example, the arrangement provides the possibility that absorbed fluids by the portion having a lower absorption capacity are lead to a second portion having a higher absorption capacity. This also provides that the feet of a person standing on the absorption having the lower absorption capacity are kept relatively dry, and as a consequence minimizing the risk of contamination of environment in which the mat used and/or the person to slip and fall.

The absorption portion having the lowest absorption capacity of the at least two absorption portions further comprises a standing area having a shape and an area size sufficient to provide a standing surface for a person to stand on.

Such an arrangement provides a fluid absorption mat that is suitable for use as a floor mat, on which a person may stand on. Furthermore, this provides the possibility that the feet of a person standing on the standing surface are kept relatively dry, and as a consequence minimizing the risk of contamination of environment in which the mat used and/or the person to slip and fall.

According to embodiments each of the at least two absorption portions may constitute at least 10%, 15% or 20% by surface area of the surface area of the fluid absorption mat.

According to one embodiment, the absorption portion having the highest absorption capacity of the at least two absorption portions may constitute at least 10% by surface area of the surface area of the fluid absorption mat. In further embodiments, the absorption portion having the highest absorption capacity of the at least two absorption portions may constitute at least 15% or 20% by surface area of the surface area of the fluid absorption mat, wherein the absorption portion having the lowest absorption capacity of the at least two absorption portions may additionally constitute at least 10% or 15% by surface area of the surface area of the fluid absorption mat.

According to other embodiments, the absorption portion having the lowest absorption capacity of the at least two absorption portions may constitute at least 50% by surface area of the surface area of the fluid absorption mat, wherein the absorption portion having the highest absorption capacity of the at least two absorption portions may additionally constitute at least 10% 15% or 20% by surface area of the surface area of the fluid absorption mat.

The minimum surface area ratio of a absorption portion provides the possibility of migration of fluids from the low absorption portion to the high absorption portion, to cover an area into which fluids can drip and flow, and/or to provide a relative high total absorption ability. Furthermore a minimum surface area ratio may also provide a standing area having a shape and an area size sufficient to provide a standing surface for a person to stand on. It also provides the possibility that the feet of a person standing on absorption having the lowest absorption capacity are kept relatively dry, and as a consequence minimizing the risk of contamination of the environment in which the mat used and/or the person to slip and fall.

According to one embodiment, the fluid absorption mat may comprise a folding line so as to facilitate folding of the mat in a predetermined manner.

Such a folding line allows the absorption portions to be turned relative to each other. This provides the possibility of folding of the mat in a predetermined manner. Furthermore, the folding line provides that the mat can be partially unfolded in a specific manner so as to provide the possibility of placing and adjusting the mat position before and during an application of the mat. This allows the possibility to adjust the position of the mat, in particular the position of an absorption portion, so as to cover an area into which fluids are dripping or flowing minimizing the risk of fluid contaminations in the medical environment. For example, in case of using the fluid absorption mat as a floor mat next to an operating table, the arrangement of a folding line provides a possibility of adjusting the mat position, when the flow of fluids from the operation table changes direction on the way down to the floor. The mat position is adjusted by folding the absorption portion having the highest absorption capacity relative to the absorption portion having the lowest absorption capacity, so that the former absorption portion is placed under the flow of fluids without changing the position of the latter absorption portion. This also provides that the absorption portion having the lowest absorption portion is kept relatively dry during the use as a floor mat due to the fact that the high absorption portion absorbs the main flow of fluids.

According to one embodiment, the folding line may provide a border between two of the at least two absorption portions.

According to one embodiment, the fluid absorption mat may comprise a fluid barrier extending along at least one edge of the mat.

A fluid barrier provides the possibility to enclose fluids within the mat, and to direct fluids within the mat, minimizing the risk of fluid contaminations in the medical environment.

According to one embodiment, at least one of the at least two absorption portions may comprise fluid migration directing means, so as to provide a migration of fluids in a direction from an absorption portion having a lower absorption capacity to an absorption portion having a higher absorption capacity.

According to one embodiment, at least one of the at least two absorption portions may comprise a super absorbent polymer.

Such a polymer provides a high absorbing capacity of the mat.

According to one embodiment, the absorption portion having the highest absorption capacity of the at least two absorption portions may comprise a super absorbent polymer.

The super absorbent polymer provides a high absorption capacity, which in turn provide a migration of fluids from absorption portion having the lowest absorption capacity to the absorption portion having the highest absorption capacity.

According to one embodiment, each absorption portion comprising a super absorbent polymer may comprise a fluid distribution means.

The fluid distribution means secure the possibility that fluids can migrate through and/or be spread over the absorption portion comprising the super absorbent polymer. For example, this secures that absorbed fluids by the absorption portion having the lowest absorption capacity can migrate from this absorption portion to the absorption portion having the highest absorption capacity, the latter comprising the super absorbent polymer and the channels, and further be spread over the high absorption portion with no risk of blocking the migration by fluid contact with the super absorbent polymer.

According to one embodiment, at least one of the at least two absorption portions comprises cellulose.

Cellulose provides an absorbing capacity of the mat and a material that may provide a standing surface.

According to a second aspect of the invention there is provided a use of a fluid absorption mat as disclosed above in a medical environment and wherein the fluid absorption mat is applied in an area into which fluids can drip or flow, and/or from which fluids are to be absorbed.

The use of a fluid absorption mats having several absorption portions provides a high fluid absorption capacity, and reduces or eliminates the risk of fluid leakage and/or contamination of an environment in which the mat is used. The use of such a mat also reduces or eliminates the risk of a mat or a surrounding area, in which the mat is used, being slippery.

According to one embodiment, a fluid absorption mat may be used as a floor mat that is applied to a medical room floor in an area into which fluids can drip or flow and on which a person is to stand, wherein the absorption portion having the lowest absorption capacity among the at least two absorption portions forms an standing area having a standing surface on which a person is to stand.

Use of the fluid absorption mat as a floor mat provides an absorption portion having a low absorption capacity with outer facing surfaces that reduces the risk of the portion being slippery when pressure, such as the weight of a person, is exerted on the absorption portion. This also provides that the feet of a person standing on the standing surface are kept relatively dry, and as a consequence minimizing the risk of contamination of environment in which the mat used and/or the person to slip and fall.

According to one embodiment, the use of the fluid absorption mat may provide that the absorption portion with the highest fluid absorption capacity among the at least two absorption portions is to be placed outside the standing area. In a further embodiment, the absorption portion with the highest fluid absorption capacity among the at least two absorption portions may be placed in front of a person standing on the standing surface.

The use of such an arrangement also provides the advantages as noted above concerning the use as a floor mat.

The invention will now be explained in more detail below with reference to the attached drawings showing embodiments of the invention.

DESCRIPTION OF EMBODIMENTS

According to the present invention a fluid absorption mat for absorption of fluids, such as absorption of body fluids and irrigation solutions (flushing agents), in medical room environments is provided. Furthermore, the mat can be a disposable mat, which means mat is to be discarded after use, and not cleaned and used again.

Figure 1:
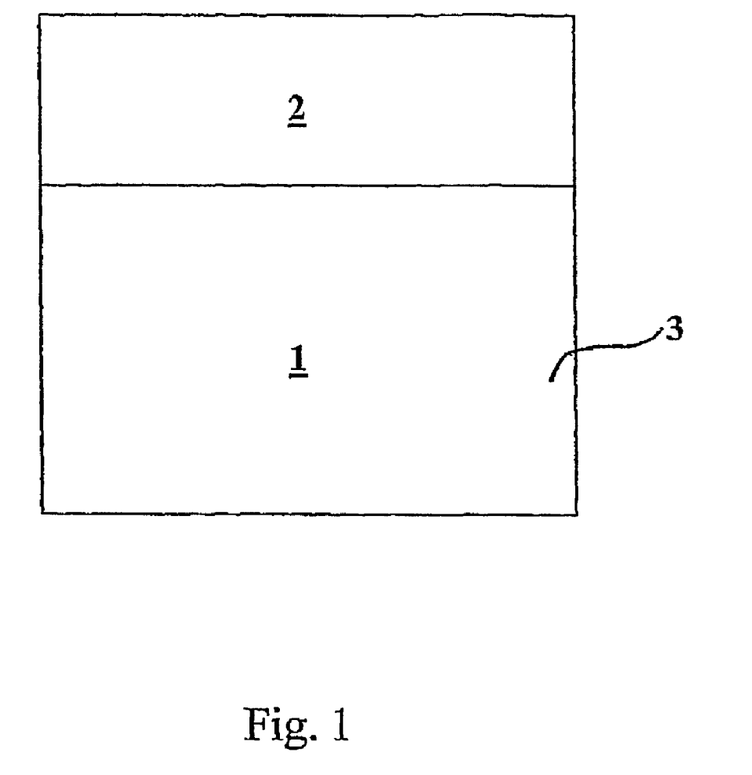
FIG. 1 is a schematic top plan view showing one embodiment of a fluid absorption mat.

FIG. 1 shows a schematic top plan view of a fluid absorption mat being an essentially planar mat having at least one fluid absorption layer and two absorption portions 1,2 presenting substantially juxtaposed projections on a principle plane of the mat. The two absorption portions 1,2 present different absorption capacities. As shown in FIG. 1, the mat comprises two rectangular absorption portions 1,2. In the following detailed description, the absorption portion 1 having the lowest absorption capacity is denoted as a low absorption portion 1. Similarly, the absorption portion 2 having the highest absorption portion is denoted as a high absorption portion 2. The low absorption portion 1 provides an absorption capacity of from 0.1 to 10, typically 1.0 liter of saline (0.9% NaCl) per square meter. The high absorption portion 2 provides an absorption capacity of from 1 to 50, typically 25 liter of saline (0.9%) per square meter. Even higher absorption capacities than 50 liter of saline per square meter might be plausible.

The absorption portions 1,2 may be joined together by an adhesive, hot melt adhesive, heat-sealing, ultrasonic sealing or any type of sealing by sewing as discussed below. They may be joined together in a partially planar overlapping manner of the planar absorption portions or by attaching the portions edge to edge. Accordingly, the mat can be produced by joining separate absorption portions 1,2 by attaching one edge of an absorption portion to one edge of another absorption portion, in an edge-to-edge manner or in a partially planar overlapping manner. The absorption portions may in turn be enclosed in between two layers that form a cover. Furthermore, the mat may also be produced as a single unit, wherein the absorption portions 1,2 are comprised in the single unit. For example, the fluid absorption layer or layers of the absorption portions 1,2 may be attached to a common supporting layer or produced as one unit by any other means known to skilled man in the art (not shown). Such a unit may in turn be enclosed in between two layers that form a cover (e.g. see below and FIG. 6).

The low absorption portion 1 of the mat provides an outer facing surface 3 on which a person can stand on without the risk of slippering, for example. This is provided by the surface structure and by the absorption material of the low absorption portion. Furthermore, any fluid absorbed by the low absorption portion 1 will have a tendency to migrate to the high absorption portion, providing the possibility of a dry outer facing surface 3 within the low absorption portion, even when pressure, such as the weight of a person, is exerted on the latter. The possibility of keeping the upper facing surface 3 dry also provides less risk of contamination of a surrounding area of the fluid absorption mat.

Figure 2:
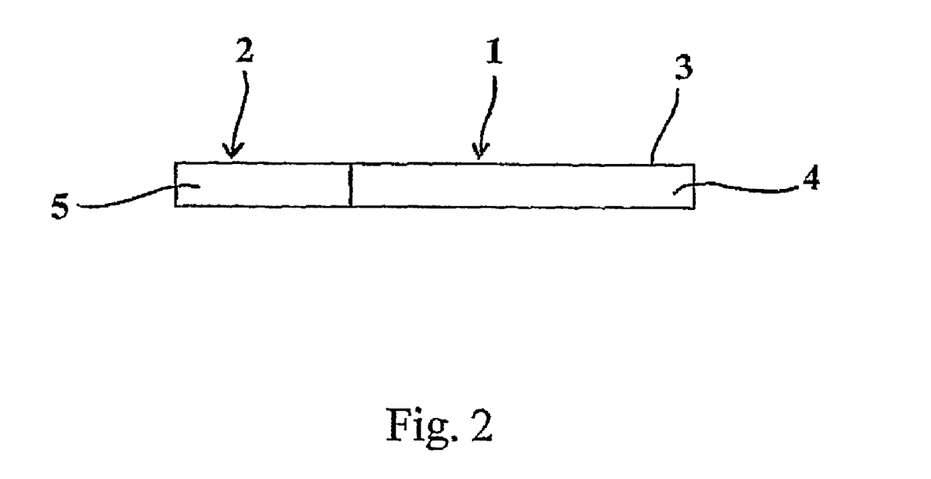
FIG. 2 is a schematic side view showing one embodiment of a fluid absorption mat.

FIG. 2 shows one embodiment of a fluid absorption mat as seen form the side, which comprises the low absorption portion 1 and the high absorption portion 2. Each portion 1,2 comprises an absorption layer 4,5.

The absorption layer 4 of the low absorption portion 1 may be composed of cellulose, rayon, vegetable fibers, synthetic fibers, such as olefin plastics, polyester or polyamide plastics, or combinations thereof. Furthermore, the absorption layer 4 of the low absorption portion 1 may be in the form of an air-laid, a spunlaced, a woven or non-woven material, such as spunbond, SMS or needle punched, or combinations thereof. Other absorption materials or forms known to the person skilled in the art, which are suitable for forming the absorption layer 4 of the low absorption portion 1 and which provides an outer facing surface 3 of the low absorption portion 1 of the mat that reduces or eliminates the risk of the mat being slippery when pressure, such as the weight of a person, is exerted on it, may be used. As also should be appreciated by the skilled man in the art, the low absorption portion 1 may comprise additional absorption layers.

The absorption layer 5 of the high absorption portion 2 may comprise a super absorbent polymer, such as a crosslinked sodium polyacrylate, a crosslinked copolymer containing sodium polyacrylate and polyvinyl alcohol, or a modified carboxymethyl cellulose (CMC). The super absorbent polymer may be in the form of powder or fibers. Such a polymer can absorb up to around 200 times its own weight of distilled water, and around 60 times its own weight of saline (0.9% NaCl solution). The super absorbent polymer may be integrated within and/or laid in between tissue paper, cellulose in fiber form, uncompressed or compressed, with or without water as a binder of the cellulose fibers, synthetic fibers based on, for example, olefin plastics, polyester plastics or polyamide plastics, molten powder based on, for example, olefin plastics, polyamide plastics or copolymer plastics containing polyamides, or a hot melt material, based on, for example, elastomers and olefin plastics. The material in which the super absorbent material is integrated and/or laid in between binds and retains the polymer within the absorption layer. Furthermore, other materials known to the person skilled in the art, into which the super absorbent polymer can be integrated and/or laid in between, that binds and retains such a polymer, may be used. Other absorption materials known to the person skilled in the art, which are suitable for forming the absorption layer of the high absorption portion, may also be used. As also should be appreciated by the skilled man in the art, the high absorption portion 2 may comprise additional absorption layers.

Typically, the size of the fluid absorption mat is adapted to the application area for which the mat is intended to be used. For example, a mat for use as a floor mat preferably have a standing area within the low absorption portion 1 having a shape and area size sufficient to provide a standing surface 3 which allows a person to stand on it, and wherein the high absorption portion 2 has a size and shape sufficient to cover an area into which fluids can drip or flow, and/or to provide a sufficient migration of fluids from the low absorption portion 1 to the high absorption portion 2. Normally the mat can be from around 30×30 cm to around 200×250 cm. For example, a typical floor mat would be around 100×110 cm (when the mat is unfolded), of which the standing area constitutes around 100×75 cm, and of which the area corresponding to high absorption portion 2 constitutes around 100×37 cm. According to embodiments, the high absorption portion 2 may constitute at least 10%, 15%, 20% or 30% by surface area of the total surface area of all portions, so as to provide the possibility of sufficient migration of fluids from the low absorption portion 1 to the high absorption portion, and to cover an area into which fluids can drip and flow, and to provide a relative high total absorption ability. According to embodiments, the low absorption portion 2 may constitute at least 10%, 15%, 20%, 30%, 40% or 50% by surface area of the total surface area of all portions, so as to provide an area into which fluids can drip and flow, and to provide a standing area 3 having a shape and an area size sufficient to provide a standing surface 3 for a person to stand on, for example.

Figure 3:
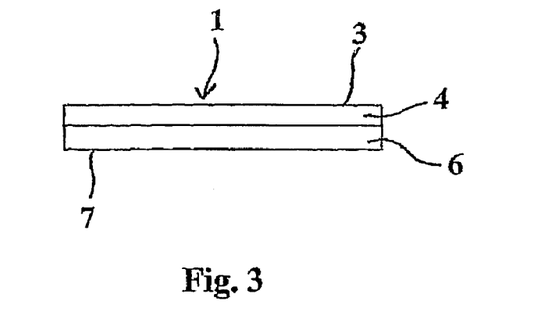
FIG. 3 is a schematic side view showing one embodiment of an absorbing portion.

FIG. 3 shows one embodiment of the absorption portion 1 of the mat that is comprised of two layers 4,6, namely one absorption layer 4 and one fluid impermeable layer 6. Such an arrangement of an absorption portion 1 may typically be used for the low absorbing portion 1. When used as a floor mat, the fluid impermeable layer 6 faces the floor area on which the mat is placed. The fluid impermeable layer 6 may be comprised of a olefin plastic, such as ethylene plastics, propylene plastics or the like, a polyester plastic, a polyamide plastic or any compounds thereof. The fluid impermeable layer 6 may further comprise additives such as ethylene butyl acrylate (EBA) in order to make the layer softer, more flexible and tougher. Furthermore, in one embodiment the fluid impermeable layer 6 may have an outer facing surface 7 that is provided with a rough surface structure and/or an antiskid agent in order to provide an antiskid (non-slip) surface, which has a sliding friction against a surface, such as a floor surface. "Surface structure" here means the three-dimensional structure of the surface 7. Other polymer materials and additives known to the person skilled in the art, which are suitable for forming a fluid impermeable layer 6 and which can be used in contact with the absorption layer 4,5 and with the surface on which the mat is to be placed, such as a floor surface in a medical room environment, may also be used.

Figure 4:
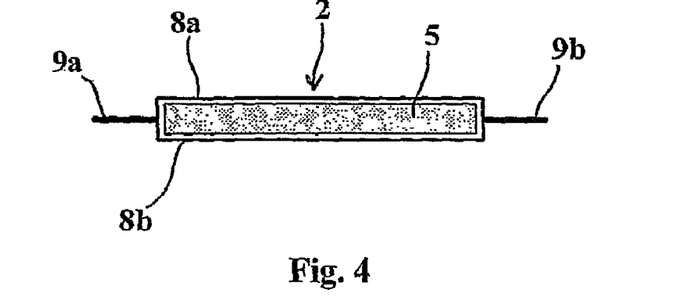
FIG. 4 is a schematic side view showing one embodiment of an absorbing portion.
Figure 5:
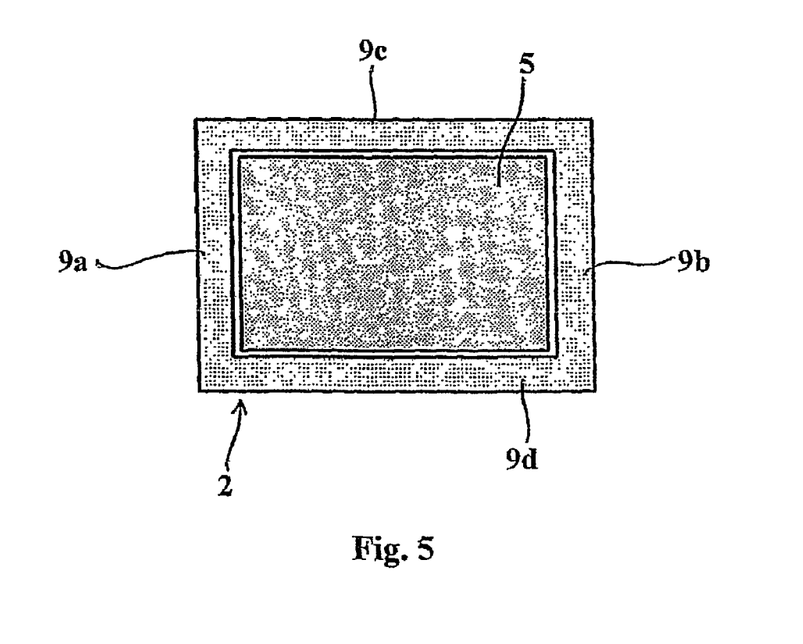
FIG. 5 is a schematic top view showing the embodiment according to FIG. 4.

As is seen in FIGS. 4 and 5, the high absorption portion 2 of the mat may be comprised of an intermediate layer 5 containing a high absorption material, which is enclosed in between two layers 8a,8b that are held together by sealing means at the edges 9a-d of these layers 8a,8b surrounding the intermediate layer 5, wherein the edges 9a-d and the sealing means form a sealer portion 9a-d. The enclosing layers 8a,8b are provided to enclose and retain the absorption intermediate layer 5 as well as enclose and retain absorption material and absorbed fluids, e.g. a gel of super absorbent polymer. At least one of the enclosing layers 8a,8b may comprise a material that is fluid permeable. The enclosing layers 8a,8b may comprise a non-woven material based on, for example olefin plastics, polyester plastics or polyamide plastics, or any mixtures thereof, a spunlaced material based on, for example, olefin plastics, polyester plastics or rayon or any mixtures thereof, or an air laid material based on, for example, cellulose combined with an adhesive of, for example, ethylene vinyl acetate, latex or synthetic fibers of, for example, olefin plastics, polyester plastics or polyamide plastics or any mixtures thereof. The layer material may also be comprised of a net-reinforced tissue paper, a perforated film material based on, for example, olefin plastics and/or polyester plastics, or a woven material of, for example, wool, cotton, olefin plastics, polyester plastics or polyamide plastics or any mixtures thereof. The layer material may also be comprised of combinations of any of the foregoing materials. Other materials known to the person skilled in the art, which are fluid permeable and suitable for enclosing and retaining the absorption intermediate layer, may also be used for at least on of the layers 8a,8b. The sealing means may be provided by means such as an adhesive, tape, hot melt adhesive, heat-sealing, ultrasonic sealing or any type of sealing by sewing. Other sealing means known to the person skilled in the art, which are suitable for sealing the edges of the high absorption portion 2 and the enclosure layer material in use, may also be used As may also be illustrated by FIGS. 4 and 5, the absorption material of the low absorption portion 1 may also form an intermediate layer 5 that is enclosed in layers 8a,8b, that reduces the risk of the low absorption portion 1 being slippery when pressure, such as the weight of a person, is exerted on it. The material of at least one of the outer facing layers 8a,8b may be composed of an material that is fluid permeable, while providing that any absorbed fluids and the absorption material is retained in the absorption layer, and that provides rigidity to the low absorption portion 1 of the mat. One example of a suitable material for such an outer facing layer 8a,8b is a felt material, such as a thin paper machine felt. In such a case the low absorption portion 1 may comprise a super absorbent polymer as is discussed in connection with the high absorption portion 2 of the mat. When used as a floor mat, the felt material may constitute at least the upper layer 8a.

Figure 6:
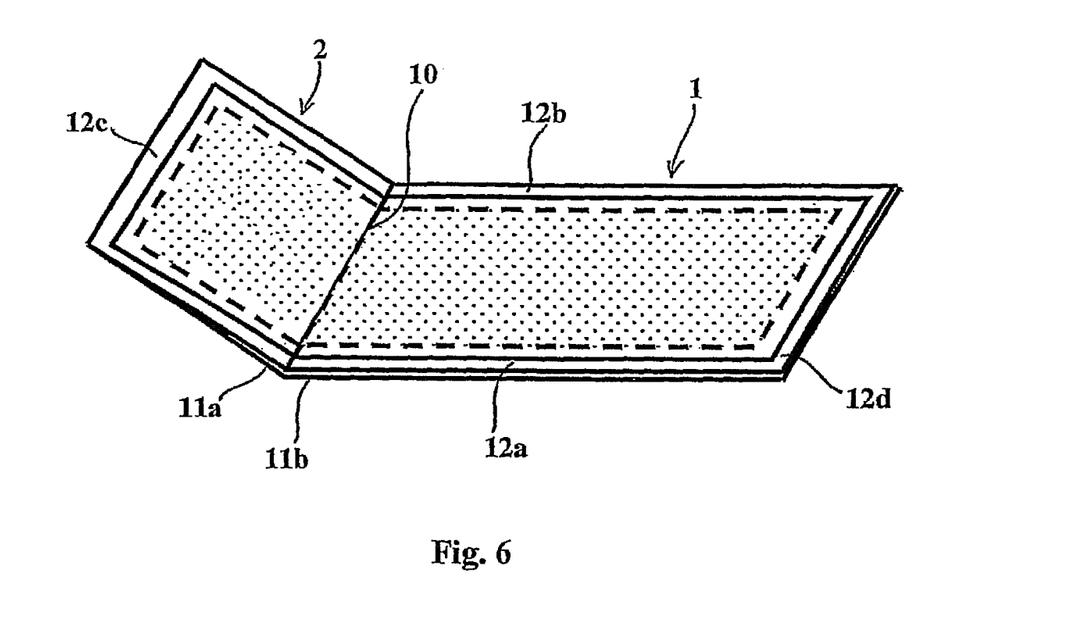
FIG. 6 is a schematic perspective view showing one embodiment of a fluid absorption mat having a folding line.

According to one embodiment, the portions 1,2 are connected to each other via a folding line 10 localized at a border 10 between the two portions 1,2 and indicated as a straight line 10 dividing the two portions 1,2 in FIG. 6. Such a folding line allows the portions 1,2 to be turned relative to each other as seen in FIG. 6. This provides the possibility of folding of the mat in a predetermined manner. Furthermore, the folding line 10 provides that the mat can be partially unfolded in a specific manner so as to provide the possibility of placing and adjusting the mat position before and during an application of the mat. For example, the low absorption portion 1 can be placed on the floor of a medical room so as to allow a person to stand on this portion 1, and the high absorption portion 2 can placed in an angle relative the low absorption portion 1 next to and bearing against a hospital bed or an operating table in front of a person standing on the standing surface 3 of the low absorption portion 1. During the application, the position of the high absorbing portion 2 can be adjusted. This allows the possibility to adjust the position of the mat so as to cover an area into which fluids are dripping or flowing minimizing the risk of contamination of the person standing on the mat, for example.

FIG. 6 illustrates one embodiment of a mat having a folding line, wherein the absorption portions 1,2 are comprised in one single unit that is enclosed in between two layers 11a,b being held together by sealing means at the edges 12a-d, wherein the layers 11a,b form a cover 11a,b (similar to the cover as discussed above in connection to FIGS. 4 and 5). The folding line 10 may be provided by compressing the unit along the border 10 between the absorption portions 1,2, or by prefolding of the unit.

Figure 7:
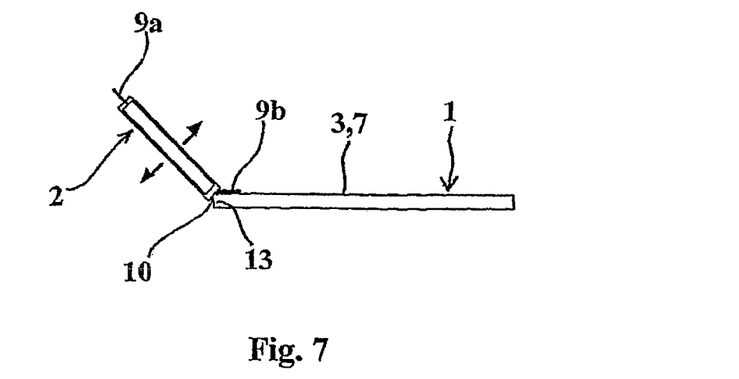
FIG. 7 is a schematic side view showing one embodiment of a fluid absorption mat having a folding line.

According to one embodiment as is illustrated in FIG. 7, the folding line 10 may wholly or partially be provided by attaching the sealer portion 9b at one edge 9b of the high absorption portion 2 to and along one edge 13 of the low absorption portion 1. This attachment provides both a way to unite the two portions 1,2 into one mat, wherein the absorption portions 1,2 are in fluid contact with each other, and a way to form the folding line 10. The different absorption portions 1,2 are preferably in close contact with each other. The attachment may be provided by means such as a tape, hot melt adhesive, heat-sealing, ultrasonic sealing or any type of sealing by sewing.

Other means of providing a folding line 10 known to the person skilled in the art, which are suitable for forming a folding line 10 in the border 10 between the two absorption portions 1,2 and which are suitable in the application in use, may also be used.

Figure 8:
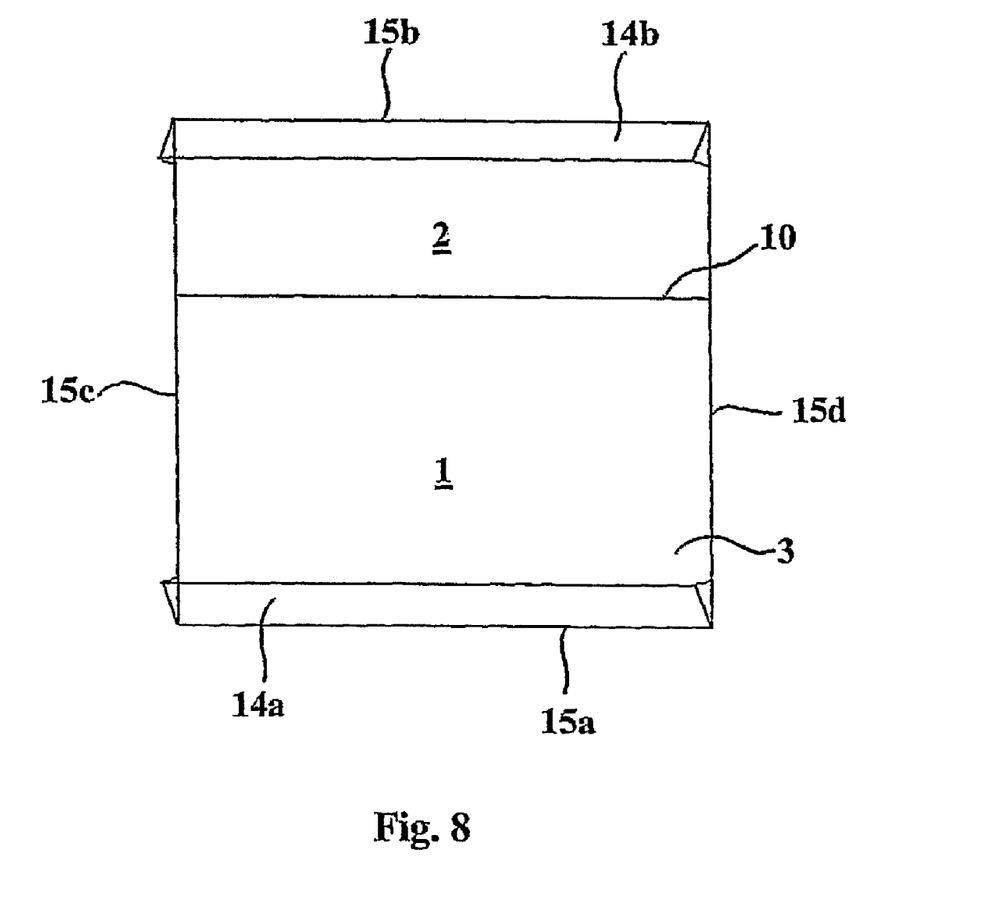
FIG. 8 is a schematic top view showing one embodiment of a fluid absorption mat that is provided with fluid barriers.

FIG. 8 shows one embodiment of the fluid absorption mat in which fluid barriers 14a,14b, are provided at opposite edges 15a,15b, of the mat, wherein one 14a is arranged at one edge 15a of the low absorption portion 1 and the other 14b one is arranged at one edge of the high absorption portion 2. The fluid barriers 14a,14b, provide the possibility to enclose fluid within the mat. As is evident for the person skilled in the art, selected edges 15a-d as well as all edges 15a-d of the mat can be provided with fluid barriers 14a,14b. The fluid barriers 14a,14b, as seen in FIG. 8 are formed as pockets. The pockets may be comprised of a hydrophobic material or a high absorption material. The fluid barriers 14a,14b, can also be arranged as hydrophobic or high absorption portions that are arranged along selected edges 15a-d of fluid absorption mat, or in any other way is evident for the person skilled in the art.

Figure 9:
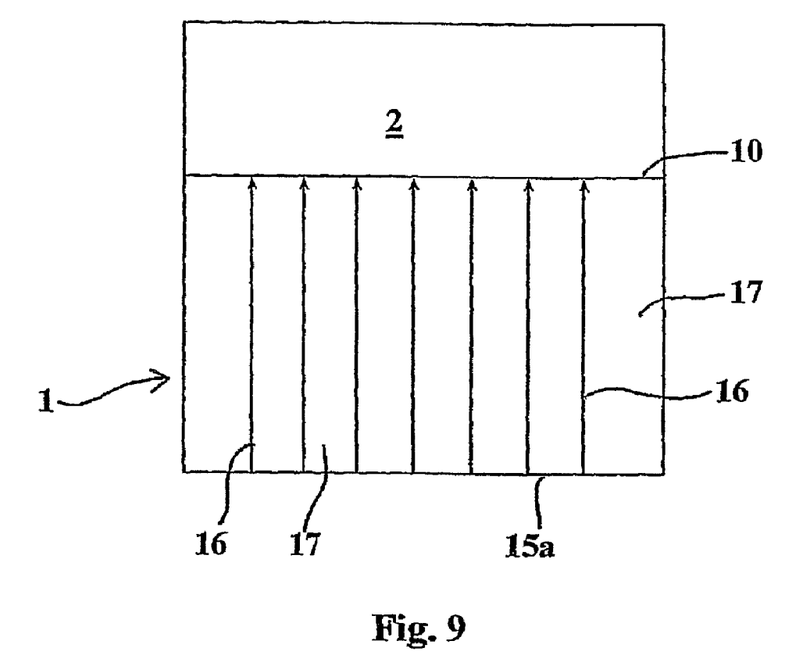
FIG. 9 is a schematic top plan view showing one embodiment of a fluid absorption mat that is provided with fluid migration directing means.

FIG. 9 illustrates one embodiment of fluid migration directing means 16,17 for directing the migration of fluids from the low absorption portion 1 to the high absorption portion 2. The means 16,17 may comprise hydrophobic strips 16 indicated as lines 16 having arrowheads in FIG. 9 running from an edge 15a of the low absorption portion 1 to an opposite edge 10 of the low absorption portion 1 that is juxtaposed the high absorption portion 2. The hydrophobic strips 16 divide the low absorption portion 1 in alternating absorption sections 17 and non-absorption sections providing absorption channels 17 being parallel to the strips 16 The channels 17 provides a way to direct the migration of fluids from the low absorption portion 1 of the mat to the high absorption portion 2 of the mat, and in addition minimizing fluid spreading within the low absorption portion 1. Alternatively, it is also possible to provide the strips 16 with openings providing a possible way of controlled fluid spreading (distribution) within the low absorption portion 1, in case of higher amounts of absorbed fluid in a local area of the mat, so as to keep the mat relatively dry (not shown).

According to one embodiment of the fluid absorption mat, the fluid migration directing means 16,17 for directing the migration of fluids from the low absorption portion 1 to the high absorption portion 2 may be provided by an absorption material density gradient or absorption material thickness gradient within the low absorption portion 1. As may also be illustrated by FIG. 9, the density or the thickness may increase from the edge 15a of the low absorption portion 1 to the opposite edge 10 of the low absorption portion 1 that is juxtaposed the high absorption portion 2. It will be appreciated that any other means 16,17 providing a direction of migration known to the person skilled in the art may be used.

Figure 10:
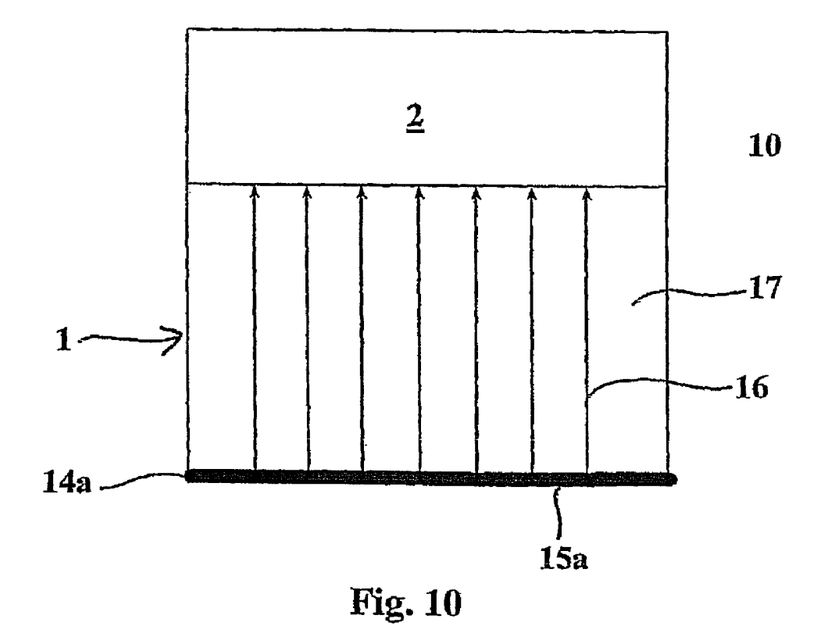
FIG. 10 is a schematic top plan view showing one embodiment of a fluid absorption mat having combined the features of the mats as shown in FIGS. 8 and 9.

FIG. 10 illustrates one embodiment the fluid absorption mat having both a fluid barrier 14a and fluid migration directing means 16,17 as discussed above. In FIG. 10 the fluid barrier 14a is shown as a hydrophobic portion extending along one edge 15a of the low absorbing portion 1. As should be appreciated any combination of fluid barriers 14a,14b and fluid migration directing means 16,17 as is evident for the skilled man in the art may be used.

Figure 11:
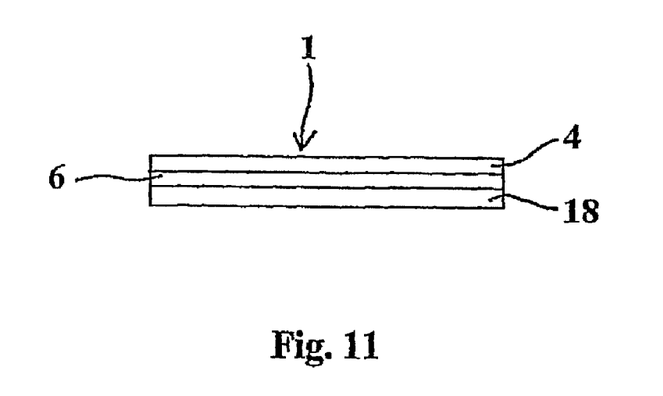
FIG. 11 is a schematic side view showing one embodiment of an absorption portion.

In FIG. 11 one embodiment of an absorption portion 1 is shown, the portion 1 comprising three layers 4,6,18, namely two outer facing absorption layers 4,18, and in between an intermediate fluid barrier layer 6. The arrangement provides an improved absorption of fluids in an area surrounding the mat. This arrangement may be suitable for providing the low absorption portion 1. The materials of the layers 4,6,18 are similar to the ones 4,6 as discussed in connection with FIGS. 2 and 3 above.

Figure 12:
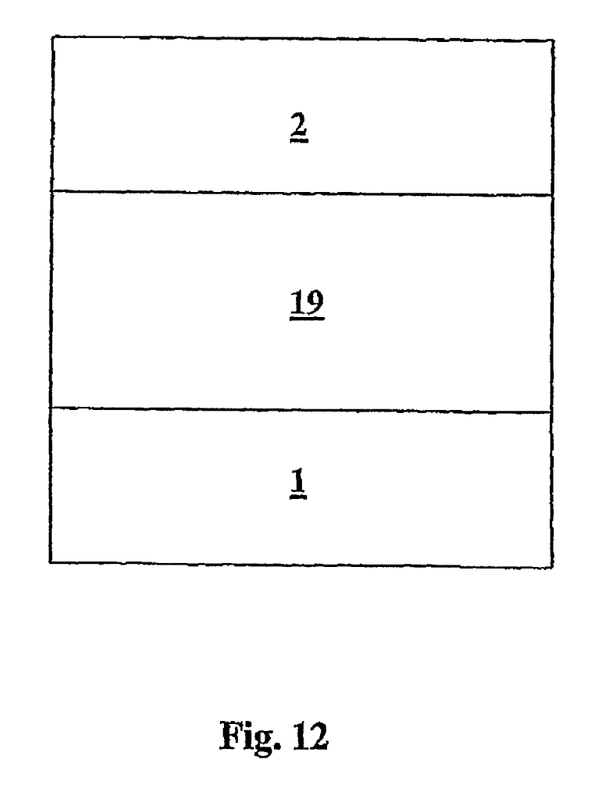
FIG. 12 is a schematic top plan view showing one embodiment of a fluid absorption mat.

According to one embodiment, three juxtaposed absorption portions 1,2,19 are arranged in a sequence as follows: a low absorption portion 1, a medium absorption portion 19 and a high absorption portion 2 (see FIG. 12). The arrangement provides a gradient that forces fluids in an absorption portion 1,19 having a lower absorption capacity to migrate to an absorption portion 2,19 having a higher absorption capacity. As should be appreciated by the skilled man in the art from the disclosure above, a folding line 10 can be provided between any of the absorption portions 1,2,19.

Figure 13:
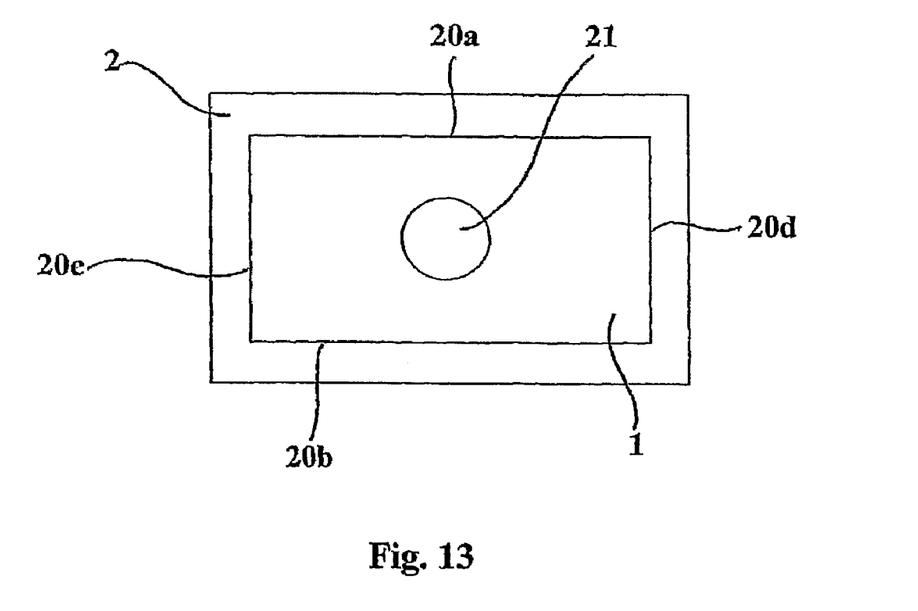
FIG. 13 is a schematic top plan view showing one embodiment of a fluid absorption mat suitable as a surgical drape.

According to one embodiment of the fluid absorption mat, the at least two juxtaposed absorption portions 1,2 may comprise a low absorption portion 1 that is arranged in the center of the mat, and a high absorption portion 2 extending along and juxtaposed the edges 20a-d of the low absorbing portion 1 (see FIG. 13). The low absorption portion 1 may also comprise an opening 21 in the center of the portion 1. Such a mat is suitable for use as a surgical drape, e.g. a surgical drape to be used during a caesarian procedure, wherein the opening 21 is placed in connection to the caesarian section of the body. This provides for example a way to direct fluids from the caesarean section to the high absorbing portion 2. In addition, the surgical drape may comprise a fluid barrier means 14a, 14b, along at least one of the edges 20a-d (fluid barriers have been discussed above).

Figure 14:
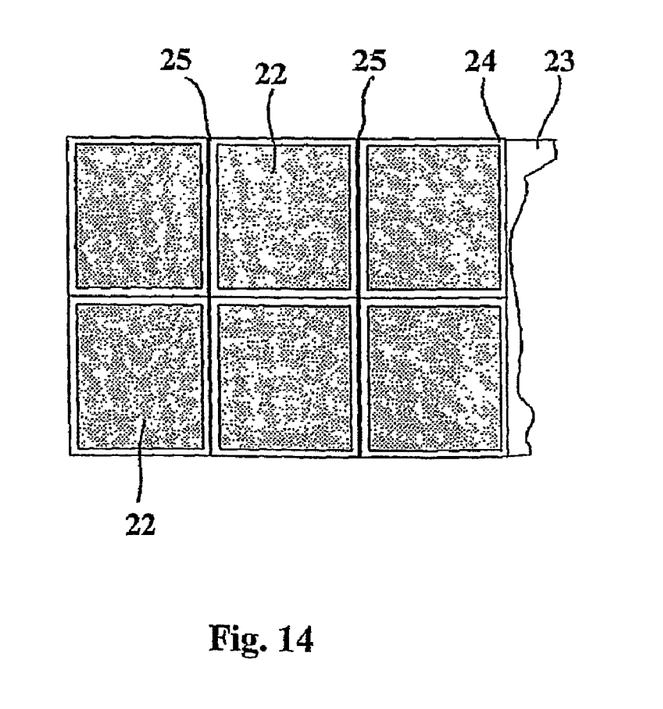
FIG. 14 is a schematic top plan view showing one embodiment of an absorption portion being divided in absorption sections.

As shown in FIG. 14, at least one absorption portion 1,2,19 of the fluid absorption mat is arranged in absorption sections 22 that are separated in a plane, substantially parallel to a principle plane of the at least one absorption portion 1,2,19. Each absorbing section 22 may comprise an absorption material such as a super absorbent polymer and other components as discussed above. The sections 22 may be seen absorption pillows sequentially arranged in rows within the at least one absorption portion 1,2,19. The sections 22 may be enclosed in between two layers 23,24 forming a cover. The two layers are held together by sealing means, such as a joint, in between each section 22 forming non-absorption sections 25. The layers 23,24 may be comprised of, for example, plastics such as polyester plastics, or a felt material as discussed above. The non-absorbing sections 25 provide rigidity so as to provide a standing surface 3 for a person to stand on, for example. Such an arrangement of at least one of the absorption portions 1,2,19 provides the possibility to include a super absorbent polymer in, for example, the low absorption portion 1, wherein any absorbed fluids and the absorption material is retained in the absorption layer 4.

Figure 15:
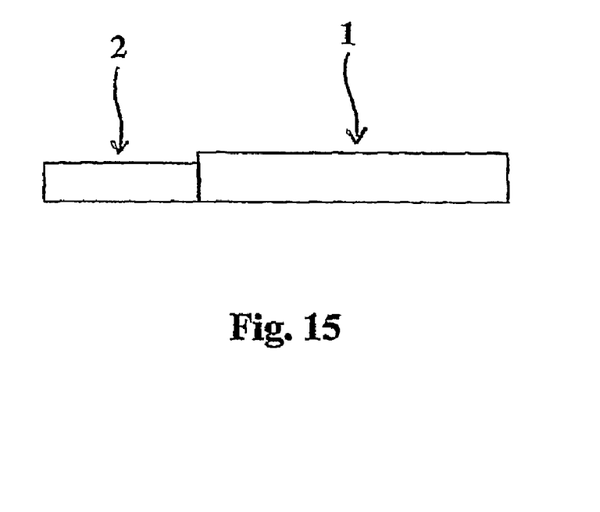
FIG. 15 is a schematic side view showing one embodiment of a fluid absorption mat, wherein the absorption portions have different thicknesses.

In FIG. 15, one embodiment is shown where the low absorption portion 1 of the mat is thicker than the high absorption portion 2 of the mat. Such an arrangement provides the possibility of fluids to migrate from the low absorption to the high absorption by gravity, when the mat is used as floor mat, for example.

Figure 16:
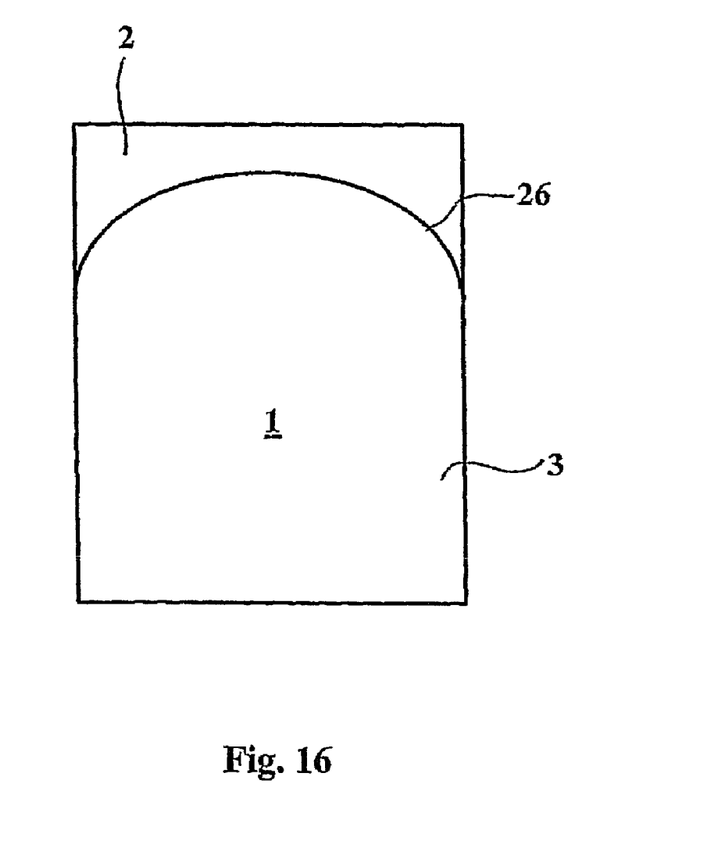
FIG. 16 is a schematic top plan view showing one embodiment of a fluid absorption mat having a curved border between the absorption portions.

FIG. 16 is a schematic top plan view showing one embodiment of a fluid absorption mat being substantially planar, and wherein the mat comprises two absorption portions 1,2, presenting substantially juxtaposed projections on a principle plane of the mat wherein the border 26 between the projections is curve formed. The border may be seen as a segment of a circle which in the middle of the mat is protruding towards the high absortion portion 2. This provides a standing surface 3 for a person to stand on which is partly surrounded by the high absorption portion 2. As also should be appreciated by the skilled man in the art, the border 26 may be adopted to any suitable form for the application in which the fluid absorption mat is to be used.

According to one embodiment, the fluid absorption mat is a substantially planar mat having a shape that may be adjusted to the area in which the mat is applied (not shown). For example, any one of the edges 15a-d of the mat may curve or straight formed depending on the application in which the mat is to be used (not shown).

According to one embodiment, the absorption portion comprising a material having a high absorption capacity such as a super absorbent polymer may be provided with fluid distribution means in form of migration channels within the absorbing material, which may be open, i.e. comprising no material, or may comprise a filling material such as cellulose in form of, for example, a fluff, tissue, spunlaced or high loft material (not shown. Such a channel may have a width of 4 to 100 mm, preferably 10 mm. The channels may partly or fully extend over the absorption portion. This provides the possibility that fluids can migrate through and/or be spread over the absorption portion comprising the super absorbent polymer. For example, this secures that absorbed fluids by the low absorption portion can migrate from the low absorption portion to the high absorption portion, the latter comprising the super absorbent polymer and the channels, and further be spread over the high absorption portion with no risk of blocking the migration by fluid contact with the super absorbent polymer.

According to one embodiment, the fluid absorption mat is a substantially planar mat having at least one fluid absorption layer 4,5,18 and wherein the mat consists of two absorption portions 1,2, presenting substantially juxtaposed projections on a principle plane of the mat and presenting different absorption capacities.

According to one embodiment, the fluid absorption mat is a substantially planar mat having at least one fluid absorption layer 4,5,18 and wherein the mat consists of three absorption portions 1,2.19, presenting substantially juxtaposed projections on a principle plane of the mat and presenting different absorption capacities.

According to one embodiment, the fluid absorption mat is a substantially planar mat having at least one fluid absorption layer 4,5,18 and wherein the mat consists of two absorption portions 1,2, presenting substantially juxtaposed projections on a principle plane of the mat and presenting different absorption capacities, and the mat further consists of a folding line 10 that provides a border between the absorption portions 1,2 and/or at least one fluid barrier 14a,14b, and/or at least one fluid migration directing means 16,17, and/or at/least one fluid distribution means.

According to one embodiment, the fluid absorption mat is a substantially planar mat having at least one fluid absorption layer 4,5,18 and wherein the mat consists of three absorption portions 1,2,19 presenting substantially juxtaposed projections on a principle plane of the mat and presenting different absorption capacities, and the mat further consists of at least one folding line 10 that provides an border between the absorption portions 1,2,19, and/or at least one fluid barrier 14a,14b, and/or at least one fluid migration directing means 16,17, and/or at/least one fluid distribution means.

According to one embodiment, the fluid absorption mat is a substantially planar mat having at least one fluid absorption layer 4,5,18 and wherein the at least two portions 1,2,19 consists of two absorption portions 1,2, presenting substantially juxtaposed projections on a principle plane of the mat and presenting different absorption capacities, and wherein any of two absorption portions 1,2 may constitutes a minimum surface area of the surface area of the fluid absorption mat as disclosed above.

According to one embodiment, the fluid absorption mat is rectangular or square formed.

According to one embodiment, there may be provided a use of a fluid absorption mat as a surgical drape that is applied to an area into which fluids can drip or flow and/or from which fluids are to be absorbed.

Such use provides a high fluid absorption capacity in area where the surgical drape is used, and reduces or eliminates the risk of fluid leakage and/or contamination of an environment in which the mat is used. Absorbed fluids may be directed from selected areas of application such as a caesarean section.

What is claimed is:

1. A fluid absorption mat for use in a medical environment, the fluid absorption mat being a substantially planar mat having at least one fluid absorption layer, comprising:
    at least two absorption portions, disposed in side-by-side relation and presenting substantially juxtaposed projections on a principal horizontal plane of the mat, said portions presenting different absorption capacities;
    a standing area having a standing surface disposed within the absorption portion having the lowest absorption capacity of the at least two absorption portions, wherein the absorption portion with the highest fluid absorption capacity among the at least two absorption portions is outside the standing area.

2. The fluid absorption mat according to claim 1, wherein each of the at least two absorption portions constitutes at least 10% by surface area of the surface area of the fluid absorption mat.

3. The fluid absorption mat according to claim 2, wherein each of the at least two absorption portions constitutes at least 15% or at least 20% by surface area of the surface area of the fluid absorption mat.

4. The fluid absorption mat according to claim 2, wherein the absorption portion having the highest absorption capacity of the at least two absorption portions constitutes at least 15% or at least 20% by surface area of the surface area of the fluid absorption mat.

5. The fluid absorption mat according to claim 1, wherein the absorption portion having the highest absorption capacity of the at least two absorption portions constitutes at least 10% by surface area of the surface area of the fluid absorption mat.

6. The fluid absorption mat according to claim 1, wherein the absorption portion having the lowest absorption capacity of the at least two absorption portions constitutes at least 50% by surface area of the surface area of the fluid absorption mat.

7. The fluid absorption mat according to claim 1, further comprising a folding line so as to facilitate folding of the mat in a predetermined manner.

8. The fluid absorption mat according to claim 7, wherein the folding line provides a border between two of the at least two absorption portions.

9. The fluid absorption mat according to claim 1, further comprising a fluid barrier extending along at least one edge of the mat.

10. The fluid absorption mat according to claim 1, wherein at least one of the at least two absorption portions comprises a fluid migration directing means to provide a migration of fluids in a direction from an absorption portion having a lower absorption capacity to an absorption portion having a higher absorption capacity.

11. The fluid absorption mat according to claim 1, wherein at least one of the at least two absorption portions comprises a super absorbent polymer.

12. The fluid absorption mat according to claim 11, wherein each absorption portion comprising a super absorbent polymer comprises a fluid distribution means.

13. The fluid absorption mat according to claim 1, wherein at least one of the at least two absorption portions comprises cellulose.

14. The fluid absorption mat according to claim 13, wherein the absorption portion having the highest absorption capacity of the at least two absorption portions comprises a super absorbent polymer.

15. The fluid absorption mat according to claim 1, wherein the absorption portion with the highest fluid absorption capacity among the at least two absorption portions is in front of a person standing on the standing surface.

16. A method of absorbing fluids in a medical environment, comprising:
   applying a substantially planar fluid absorption mat to an area into which fluids can drip or flow;
   providing at least one absorption layer disposed within the mat, said layer having at least two absorption portions disposed in side-by-side relation on a principal horizontal plane of the mat and presenting different absorption capacities;
   providing a standing area having a standing surface disposed within the absorption portion having the lowest absorption capacity of the at least two absorption portions;
   placing the absorption portion with the highest fluid absorption capacity among the at least two absorption portions outside the standing area;
   absorbing the fluids into the fluid absorption mat; and
   directing the absorbed fluids from the absorption portion having the lowest absorption capacity of the at least two absorption portions to the portion having the highest absorption capacity of the at least two absorption portions.

17. The method of claim 16, further comprising placing the absorption portion with the highest fluid absorption capacity among the at least two absorption portions in front of a person standing on the standing surface.

* * * * *